United States Patent [19]

Usher

[11] Patent Number: 4,659,740
[45] Date of Patent: Apr. 21, 1987

[54] COSMETIC PREPARATIONS COMPRISING NOVEL ELASTIN DERIVATIVES

[75] Inventor: Thomas C. Usher, Nassau, The Bahamas

[73] Assignee: Polydex Pharmaceuticals Ltd., Nassau, The Bahamas

[21] Appl. No.: 701,960

[22] Filed: Feb. 14, 1985

[51] Int. Cl.$^4$ ............................ A61K 7/48; C09F 7/00
[52] U.S. Cl. .................................... 514/773; 514/801; 514/844; 514/847; 530/353; 260/404.5
[58] Field of Search ..... 424/70; 260/123.7, 404.5 PA; 514/801, 773, 847, 844; 530/353

[56] References Cited

U.S. PATENT DOCUMENTS

| | | | |
|---|---|---|---|
| 2,827,419 | 3/1958 | Tourtellote | 514/801 |
| 3,393,080 | 7/1968 | Erdi et al. | 514/801 |
| 3,632,350 | 1/1972 | Battista | 424/59 |
| 3,954,725 | 5/1976 | Johnson et al. | 260/123.7 |
| 4,186,188 | 1/1980 | Gumprecht | 260/123.7 |
| 4,327,078 | 4/1982 | Charlet et al. | 424/70 |
| 4,363,760 | 12/1982 | Cioca | 260/123.7 |
| 4,419,288 | 12/1983 | Cioca | 260/123.7 |
| 4,454,159 | 6/1984 | Musher | 424/59 |

FOREIGN PATENT DOCUMENTS 2540381  7/1984  France ............................ 514/801

OTHER PUBLICATIONS

Kagan et al., Chem. Abs., 1976, vol. 85, pp. 15705n.
Fieser et al., Advanced Organic Chemistry, 1961, pp. 518 & 519.

*Primary Examiner*—Dale R. Ore
*Attorney, Agent, or Firm*—I. Louis Wolk

[57] ABSTRACT

This invention relates to a cosmetic preparation which comprises novel derivatives of solubilized elastin which are fatty acid amides of elastin, and which have been found to permit deeper penetration and a higher percentage absorption of elastin into the stratum corneum of human skin.

10 Claims, No Drawings

COSMETIC PREPARATIONS COMPRISING NOVEL ELASTIN DERIVATIVES

BACKGROUND OF THE INVENTION

The skin consists of a number of overlapping layers of cells. The outermost layer of the skin is called the stratum corneum and consists of dead keratinized cells. This layer protects the skin from physical and atmospheric harm, acting as a barrier to external dangers. The stratum corneum compared with the lower layers of the epidermis, is rather dry. Lack of moisture in the lower layers of the skin results in a wrinkled and aged look. Lack of moisture in the stratum corneum, however, is even more noticeable in that this is the layer that we see. The dryness is marked by roughness, increased flakiness, and in more severe cases, cracks and actual peeling. The skin may appear reddened and even inflamed if the dryness is sufficiently acute. It has been shown, by at least one scientist, that the stratum corneum remains soft and pliable only as long as the moisture content exceeds 10%. Below this, the skin becomes hard and brittle and develops an opacity.

In the lower layers of the skin, degenerative changes occur with age whereby not only moisture is lacking, but also a major amount of lipoidal or fatty substances. In cosmetic practice, it is the outermost layer of the skin which can best be benefitted by application of external lotions and creams. If this outermost layer can be made to look plump, transparent and healthy, the overall skin texture will assume a more youthful appearance, however studies of the epidermis indicate that the stratum corneum is capable of absorbing and retaining only moisture. It will not accept lipid or fatty substances. Such materials used for moisturization of the skin have no direct effect whatever in increasing the hydration of the epidermal cells.

As the result of aging, exposure to various climatic conditions, such as sun and wind and other factors in addition to loss of moisture in the epidermal layers of the skin, it has been found that loss of elasticity and skin tone and texture may occur through degradation of certain complex polypeptides present in the skin such as elastin and collagen, among others.

Elastin is a highly cross-linked amino acid complex which is a major component of elastic fibers present in the skin and connective tissue of animals and which are responsible for their physiologic elasticity. In normal human skin, these elastic tissue proteins represent a relatively small fraction of the total dermal proteins but play an important role in maintaining or improving skin tone and structure.

The dense cross-linked structure of elastin makes it very difficult to solubilize, however, this has been accomplished by means of enzymes or by means of various types of hydrolytic procedures, as described, for example, in U.S. Pat. No. 4363760.

Attempts have been made to utilize elastin, particularly when solubilized by hydrolysis, as a component of cosmetic compositions. However, it has been found that elastin is only slightly absorbed by the skin and does not penetrate sufficiently to produce substantial benefits to the skin.

SUMMARY OF THE INVENTION

This invention relates to the discovery that solubilized or partially hydrolyzed elastin can be derivatized to produce a material having increased penetration of the epidermal layers of human skin.

In accordance with the present invention, therefore, it has been discovered that by attaching a fatty acid moiety to hydrolyzed elastin, a product is obtained which, on application to human skin, is found to provide significant penetration deeper than the surface layers of the stratum corneum with a substantial degree of penetration through the 10th to 12th layers. This is in decided contrast to the penetration achieved by application to the skin of a non-derivatized solubilized elastin.

In the study of the structure of the stratum corneum, the dermatologists have used strips of plastic adhesive tape, such as, the well known "Scotch" brand tape to remove successive layers of the stratum corneum with each piece of tape. This has been verified by staining of the cells removed by each layer followed by histological examination. For most individuals, the stratum corneum comprises about 12-18 layers of cells (sometimes considered as 10-20 layers). After this number of layers have been stripped from the same site of stratum corneum, there appears what is known as the "glistening layer" of the epidermis, which is so-called because at this layer tissue fluid starts to ooze out of the living cells.

It is believed that stripping off these layers of the stratum corneum followed by subsequent analyses of single or multiple layers gives a good indication of the degree of permeability of a material into the skin.

DETAILED DESCRIPTION OF THE INVENTION

In the case of elastin, the degree of absorption appears to be important in restoring fibrous protein to the surface layers of the skin and consequent improvement in tone and structure often accompanied by removal of small wrinkles.

In the development of the present invention, it was first determined that hydrolysed elastin, itself, did have a slight degree of permeability beyond the first and second layers of the stratum corneum but that this degree of permeability was insufficient to provide significant benefits as a skin conditioner. In order to improve the degree of penetration of elastin, it was decided to determine whether the addition of a suitable alkyl group to an N-terminal group of the elastin molecule would accomplish this. Accordingly, it was decided to attempt the attachment of a fatty acid (moiety), such as lauric acid, palmitic acid or oleic acid.

The alkylation procedure was carried out by first converting the fatty acid to the corresponding anhydride and then alkylating elastin in aqueous solution to obtain elastin-fatty acid derivative in the form of the corresponding amide or fatty acid N-acyl derivatives, such as the laurate, oleate or palmitate or mixtures thereof as desired. The resulting products were then tested for skin permeability in comparison with soluble elastin by using tritiated fatty acid moieties alkylated onto elastin as applying them to skin surfaces, and removing successive layers of skin and measuring the radioactive absorption in such layers by means of liquid scintillation spectrocopy as described in the examples herein. As the tests results demonstrate, while tritiated hydrolysed elastin with N-alkylated tritiated acetate showed some slight degree of permeability to layers of the stratum corneum below the surface, the corresponding fatty acid derivatives showed a much higher degree of penetration in the lower layers of the stratum corneum as described in greater detail below.

Elastin acetic anhydride treated, elastin lauryl anhydride treated, elastin and palmityol/oleoyl treated elastin all gave essentially identical retention profiles on standard 15 mm×180 mm BioRad P2 gel filtration beads. In each case a marker tritiated acetic acid, tritiated lauric acid and tritiated 9,10-palmitic acid each converted to the sodium salt resulted in two to three times the retention time. The longer retention time for the pure fatty acid salts indicated successful reaction between the anhydrides and elastin in each case.

Hydrolysis in 0.5 normal sodium hydroxide for thirty minutes at 60° C., failed to produce any free acid material in each case indicating that amide bonds were formed between elastin and the reacted anhydrides.

Cooling to 4° C. of a 5 or 10% preparation of lauryl elastin or palmitoyl/oleoyl elastin, resulted in turbidity indicating that these intermediate or long chain elastin derivatives had reduced water solubility. These preparations also result in some foaming activity at room temperature. This indicates some mild detergent activity. Ten percent elastin by itself does not become turbid when cooled and shows less foaming activity at room temperature.

When the derivatized elastin is incorporated in cosmetic preparations such as skin creams and utilized upon the skin for a period of days, noticeable moisturing and skin toning effects are obtained. In addition, it was found that wrinkles were often reduced or eliminated as evidence that the deep absorption of elastin was effective.

EXAMPLE 1

Penetration of the stratum corneum of human skin by elastin was determined by reacting a 5 ml sample of hydrolysed elastin (crolastin G.C. mw approximately 4000, 10% protein) with 5 ml tritiated acetic anhydride at room temperature for 48 hours to acylate some of the terminal nitrogen groups of the elastin molecule. Under these conditions, tritium acetylation is obtained at a small percentage of the active groups although most of the N-sites were probably acetylated.

The resulting tritiated product was subjected to repeated dialysis until a purified product having a specific radioactivity of 523 counts per mg was obtained.

2 mg of the product (1046 counts) was applied to 1 square centimeter of the forearm of a human and after remaining in place for 2½ hours, "Scotch" tape strippings were taken from successive layers of the stratum corneum and placed in liquid scintillation counting vials for analysis. Results obtained were tabulated as follows:

| Layers | Counts | % Distribution | Recovered ug elastin/cm$^2$ |
| --- | --- | --- | --- |
| 1–2 | 3061 | 88 | 599 |
| 3–5 | 327 | 9 | 63 |
| 6–8 | 74 | 2 | 14 |
| 9–11 | 24 | 1 | 5 |
| 12–14 | 0 | 0 | 0 |

These results showed a minor degree of penetration below the second layer of the stratum corneum. That is, while the penetration of the first two layers is measured by radioaction, counting was 88% of recovered counts, the penetration of layers 3 to 5 was only 9% of recovered counts.

EXAMPLE 2

Preparation and permeability testing of lauric acid amide of elastin (elastin laurate).

100 ml aqueous solution of hydrolyzed elastin (10% protein) are reacted with 1.1 gram of lauryl anhydride added dropwise while stirring at 40° C. for 1 hour. The reaction is then allowed to continue for 14 hours at 40° C. At the end of this time 1% of citric acid was added to this reaction mixture which was then extracted twice with 50 volumes of chloroform and the organic phase from each extraction separated to remove unreacted fatty acid. The aqueous reaction mixture was then dialysed to further remove unreacted lauric acid and lauryl anhydride. The final solution was adjusted to 5% protein (lauryl elastin).

The lauric acid amide of elastin is contained in the solution of 5% concentration.

For testing of the permeability of this product upon the human skin, the elastin is reacted with tritiated lauric anhydride and the same procedure is followed to produce an aqueous solution of the lauric acid derivative as above also at 5% concentration.

The resulting aqueous solution of tritiated elastic laurate was then tested for permeability to human skin as follows:

2 mg of the product having a radioactivity of 4021 units per minute was applied to about 1 square centimeter of forearm surface area (2 mg of protein).

1 hour later, "Scotch" tape strippings were made and counted in a liquid scintillation spectrometer. The following results were obtained:

| Layer of SC | Counts | % Distribution | Recovered ug elastin/cm$^2$ |
| --- | --- | --- | --- |
| 1–2 | 1852 | 53 | 920 |
| 3–5 | 361 | 10 | 180 |
| 6–8 | 742 | 21 | 370 |
| 9–11 | 390 | 11 | 194 |
| 12–14 | 130 | 4 | 65 |

The above results demonstrate a substantial degree of permeability of the tritiated elastin laurate down through layers 12–14 of the stratum corneum after one hour contact. Layers 6–14 sum to 36% of recovered counts.

EXAMPLE 3

Tritiated elastin palmitate/oleate was produced in the same manner as in Example 2, by reacting tritiated palmitoyl anhydride and oleoyl anhydride with solubilized elastin (10% protein). A mixture of palmitoyl/oleoyl anhydride resulted in a product with better solubility than when palmitoyl anhydride alone was used.

The product, the palmitoyl/oleoyl amide of elastin had a radioactivity corresponding to 82 counts per minute per milligram ($^3$H-9, 10-palmitate). The solution was applied directly to the skin (forearm) with a glass rod in an amount equal to about 2 mg of the product per square centimeter of skin in two separate tests at ½ hour and 1 hour exposure.

"Scotch" tape strippings were then taken of successive layers of the skin and scintillation measurements were taken of the samples removed.

The following results were noted:

| Layers | Counts | % Distribution | Recovered ug Elastin |
|---|---|---|---|
| (a) ½ Hour Exposure | | | |
| 1–2 | 8 | 40 | 98 |
| 3–9 | 12 | 60 | 146 |
| 10–12 | 0 | 0 | 0 |
| (b) 1 Hour Exposure | | | |
| 1–2 | 26 | 55 | 317 |
| 3–9 | 19.6 | 41 | 239 |
| 10–12 | 1.7 | 4 | 21 |

EXAMPLE 4

The procedure of Example 3 was carried out using a porous patch composed of Agarose (0.5%) and covered with adhesive tape on the periphery measuring 1 sq. cm impregnated with the tritiated elastin palmitate instead of application as a lotion and the patch remained in position for three hours before the "Scotch" tape strippings were removed and tested. The following results were obtained:

| Layers | Counts | % Distribution | Recovered ug Elastin |
|---|---|---|---|
| 1–2 | 6 | 13 | 75 |
| 3–9 | 30 | 64 | 375 |
| 10–12 | 11 | 23 | 137 |

As shown in the foregoing Examples 1–4, the degree of penetration represented by the radioactive count and corresponding measurement of micrograms of elastin and elastin amide absorbed in the various layers is greatly enhanced by the presence of the fatty acid groups on the molecule. It is clear that the amount and degree of penetration is also in proportion to the time of contact or exposure on the skin. In Example 3, the half hour exposure provided substantial absorption in layers 3–9 with none 10–13, while a 1 hour exposure did also indicate significant penetration in layers 10–12.

Example 4 shows the results obtained with a three hour exposure using a patch instead of lotion with high degree of penetration.

EXAMPLE 5

The fatty acid elastin amides described herein are preferably formulated into conventional types of cosmetic creams or lotions for application to human skin.

A typical skin cream comprising the elastin amide described above as produced in Example 2 is formulated as follows: (Parts by weight)

| Phase A | |
|---|---|
| Glyceryl monostearate | 5 |
| Stearic Acid | 4 |
| Isopropyl myristate | 3 |
| Cetyl alcohol | 1 |
| Lanolin U.S.P. anhydrous | 1 |
| Phase B | |
| Water | 50 |
| Glycerin | 3 |
| Triethanolamine | 1 |
| Lauric acid amide of elastin | 2 |
| Preservative (methyl paraben) | .02 |

Phase A is melted at 70° C. Phase B is preheated to about 50° C. and added slowly with stirring to molten Phase A and cooled slowly. A suitable fragrance may then be added after which it is homogenized into jars.

The above cream, when applied to skin and allowed to remain for 1–3 hours, or overnight as desired, is found to gradually improve and soften the skin after a period of several days' use and as the skin is softened and the elastin derivative is absorbed, small wrinkles are found to disappear.

EXAMPLE 6

A simple emulsion for application to skin to achieve softening and penetration with elastin may be prepared by adding 2–5 parts of the lauryl amide of elastin (Example 2) or the palmityl/oleyl amide of elastin (Example 3) to a solution of 100 parts of distilled water and 15 parts of an emulsifying agent such as propyleneglycol monostearate and a small amount of a preservative such as methyl paraben, and intimately mixing to form an emulsion.

In general incorporation of any significant proportion of the elastin fatty acid amides of this invention into conventional cosmetic preparations which are then allowed to remain on the skin for substantial periods of time, say 1–3 hours during the day, or over night, appears to result in a high degree of penetration as shown by the results obtained with tritiated materials in the above examples. Various proportions of the amides may be utilized but in general, proportions of 2–10% seem to be adequate to obtain noticeable results.

I claim:

1. A cosmetic preparation for application to the skin which comprises a fatty acid amide of solubilized elastin in which the fatty acid moiety is attached to an N-terminal group of the elastin molecule.

2. A cosmetic preparation according to claim 1 wherein the fatty acid amide is the lauric acid amide of elastin.

3. A cosmetic preparation according to claim 1 wherein the fatty acid amide is the palmitic acid amide of elastin.

4. A cosmetic preparation according to claim 1 wherein the fatty acid amide is the oleic acid amide of elastin.

5. A derivative of elastin which is capable of substantial penetration of the stratum corneum of human skin which is the reaction product of solubilized elastin with a fatty acid anhydride to produce the corresponding amide in which the fatty acid moiety is attached to the N-terminal group of the elastin molecule.

6. A method for the manufacture of a fatty acid amide of elastin having a substantial degree of penetrability of human epidermous which comprises reacting hydrolyzed elastin with a fatty acid anhydride in aqueous solution to attach the fatty acid moiety to an N-terminal group of the elastin molecule and recovering the fatty acid amide of elastin produced thereby.

7. A method according to claim 6 wherein the fatty acid anhydride is the anhydride of lauric acid and the resulting product is the lauric acid amide of elastin.

8. A method according to claim 6 wherein the fatty acid anhydride is the anhydride of palmitic acid and the resulting product is the palmitic acid amide of elastin.

9. A method according to claim 6 wherein the fatty acid anhydride is the anhydride of oleic acid and the resulting product is the oleic acid amide of elastin.

10. An amide of elastin prepared by the method of claim 6.

* * * * *